(12) United States Patent
Isear, Jr.

(10) Patent No.: US 6,368,291 B1
(45) Date of Patent: Apr. 9, 2002

(54) METHOD AND APPARATUS FOR LOWER EXTREMITY TESTING

(76) Inventor: Jerome A. Isear, Jr., 7632 Watercrest Rd., Charlotte, NC (US) 28210

( * ) Notice: Subject to any disclaimer, the term of this patent is extended or adjusted under 35 U.S.C. 154(b) by 0 days.

(21) Appl. No.: 09/651,788

(22) Filed: Aug. 30, 2000

Related U.S. Application Data

(60) Provisional application No. 60/151,857, filed on Sep. 1, 1999.

(51) Int. Cl.$^7$ .................................................. A61B 5/00
(52) U.S. Cl. ...................................................... 600/595
(58) Field of Search ............................... 600/587, 592, 600/594, 595

(56) References Cited

U.S. PATENT DOCUMENTS

| | | | |
|---|---|---|---|
| 5,335,674 A | * 8/1994 | Siegler | 600/595 |
| 5,474,086 A | * 12/1995 | McCormick et al. | 600/595 |
| 5,823,974 A | * 10/1998 | Grassi | 600/595 |
| 5,913,831 A | * 6/1999 | Breneman | 600/595 |

* cited by examiner

Primary Examiner—Max Hindenburg
(74) Attorney, Agent, or Firm—Dougherty & Clements LLP

(57) ABSTRACT

A method and an apparatus for testing the entire lower extremity as one functional unit, the apparatus comprising a horizontally planar base having a knee tripodal portion and a hip tripodal portion adjustably coupled to the knee tripodal portion by a variable length connector, a knee post fixedly attached to the knee tripodal portion and vertically extending orthogonally away from the horizontal plane of the horizontally planar base, a hip post fixedly attached to the hip tripodal portion and vertically extending orthogonally away from the horizontal plane of the horizontally planar base, a knee bar that is adjustably connected to the knee post and a hip bar that is adjustably connected to the hip post. The knee tripodal portion and the hip tripodal portion may each be releasably secured to the variable length connector by a respective locking fastener. Likewise, the knee bar may be releasably secured to the knee post and the hip bar may be releasably secured to the hip post by a respective locking fastener. The variable length connector allows the invented apparatus to be horizontally adjusted by increasing or decreasing the distance between the knee tripodal portion and the hip tripodal portion depending upon a patient's particular physical dimension, such as the distance between the hip and the knee of the patient. The knee post and the hip post allows the invented apparatus to be adjusted in height by vertically extending or retracting the knee bar and the hip bar orthogonally away from or toward the horizontal plane of the horizontally planar base to accommodate a patient's particular physical dimension, such as the distance between the knee and the ankle of the patient.

52 Claims, 9 Drawing Sheets

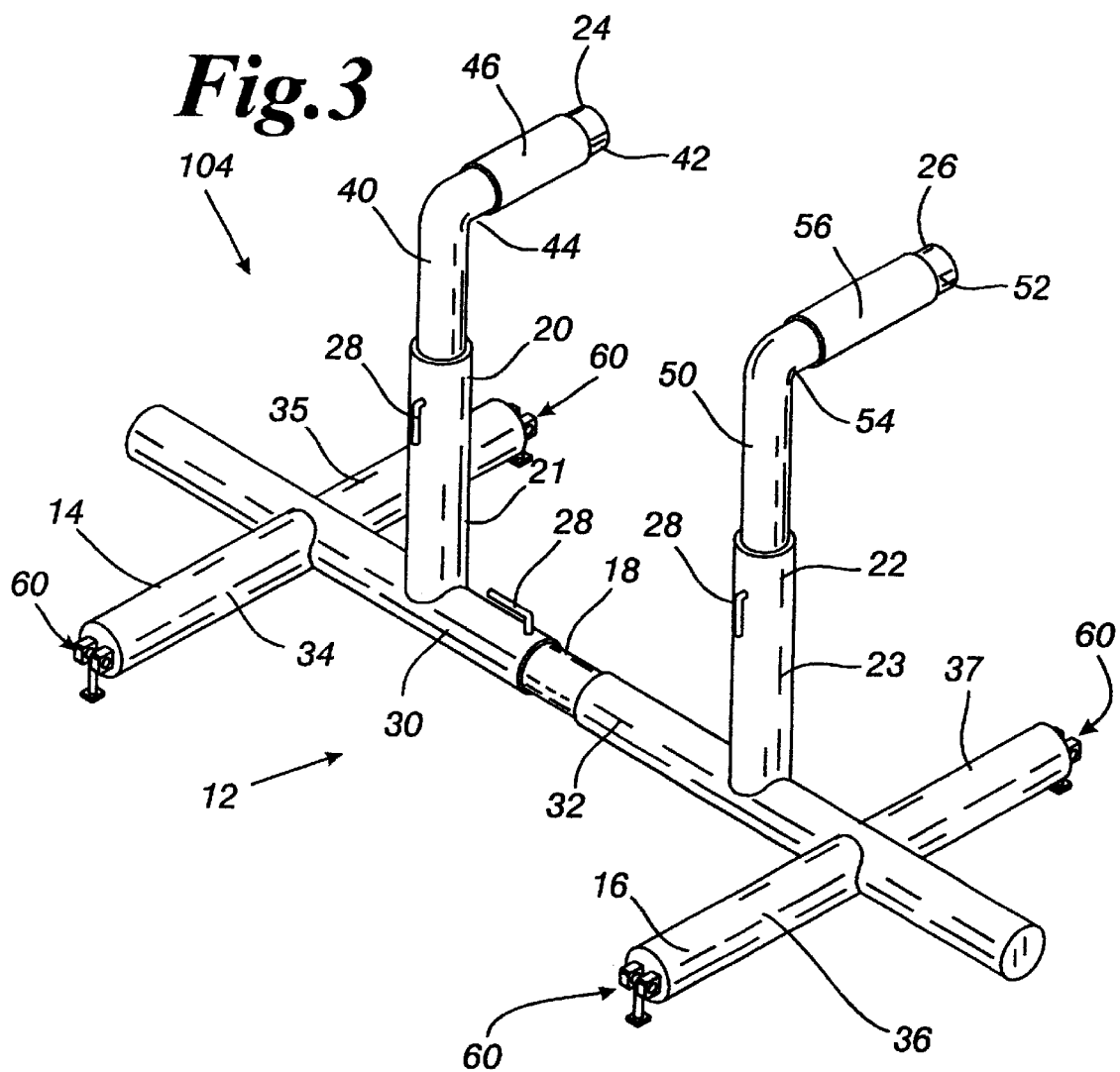
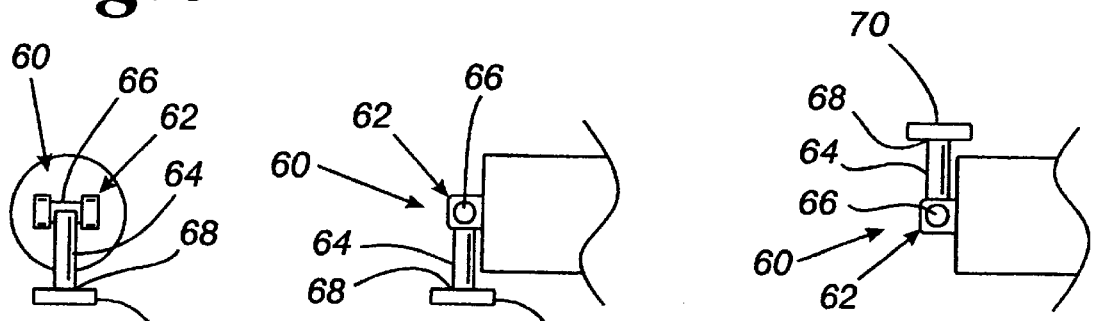
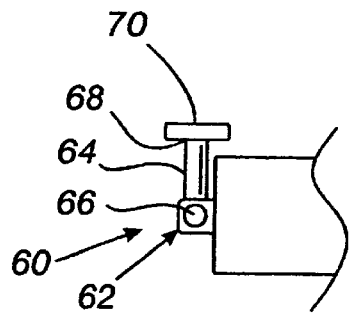

METHOD AND APPARATUS FOR LOWER EXTREMITY TESTING

CROSS REFERENCE TO RELATED APPLICATION

This application claims the benefit of U.S. Provisional Application No. 60/151,857, filed Sep. 1, 1999.

FIELD OF THE INVENTION

This invention relates generally to assessment of lower extremity function for a human body, and more particularly to a method and an apparatus for assessing muscle strength, balance, endurance, coordination for a human body.

BACKGROUND OF THE INVENTION

Physical rehabilitation is an important and oftentimes necessary step for improving an individual's state of health, particularly after the individual's body has undergone a traumatic event, such as an injury or surgical procedure. Rehabilitation of the lower extremity of the body is commonplace, particularly in light of injuries suffered from work related injuries or participation in any of numerous sports requiring lower extremity contribution, such as running (i.e., baseball, basketball, football, soccer and tennis), skiing (water skiing or snow skiing), cycling, weight lifting, roller blading and hockey. Furthermore, rehabilitation after a lower extremity injury or surgical procedure is critical for returning a patient to full functional capacity. Proper and effective rehabilitation of the lower extremity of the body requires continual assessment of the lower extremity function. For example, standardized data relating to the capabilities of muscle groups in the lower extremities are needed in order to properly guide a patient's rehabilitative treatment after suffering from a lower extremity injury (i.e., hip, leg, knee, ankle or foot injury) or following a lower extremity surgical procedure (i.e., reconstructive knee surgery) and also to properly evaluate the patient's overall physical ability to return to functional activities such as sports, work and general activities of daily living. Lower extremity function is generally evidenced by the integration of strength, balance, endurance and coordination.

Lower extremity function has been studied for many years. Several clinical tests have been used to assess lower extremity function after suffering from lower extremity injuries. For example, much discussion has focused on the most effective approach to rehabilitation of a lower extremity (i.e., hip, leg, knee, ankle or foot injury), specifically the use of open kinetic chain (OKC) exercises and closed kinetic chain exercises (CKC). Similarly, much discussion has focused on whether OKC exercises or CKC exercises are the more valid and reliable test for evaluating a patient's overall ability to return to functional activities such as sports, work and activities of daily living, without further risk of injury. Much controversy exists in the literature as to the correlation between these two testing philosophies. Several studies have demonstrated a positive correlation between OKC and CKC testing, while others have demonstrated little if any correlation. As is the case with rehabilitation philosophies, OKC and CKC testing methods have both been utilized. Recently however, the use of CKC exercises has been advocated due to many documented advantages over OKC exercises.

Of the CKC tests performed, hop tests are most commonly used to assess lower extremity function. The hop test provides an assessment of functional strength, balance, endurance and coordination of the entire lower extremity. The hop test involves single-leg hopping across a floor. Unfortunately, the hop test can not be safely implemented until the later stages of the rehabilitation process. This is in part due to the requirement, associated with the hop test, that the muscles, which are still undergoing rehabilitation, must exhibit not yet attainable explosive exertion upon vertical takeoff. This is also in part due to the tremendous and potentially damaging forces that the muscles, ligaments, joints, cartilage and surrounding supportive tissues, which are still undergoing rehabilitation, must endure upon gravitational impact. Another CKC test is based on an inclined squat or leg press test. Even though this test assesses strength and endurance in the CKC environment, the inclined squat or leg press test does not take into account the balance issue and the coordination issue because the patient is resting on the inclined squat or leg press machine.

Of the OKC tests, isokinetic testing remains the standard mainly because of the ability to perform isolated lower extremity muscle strength testing. The isokinetic test provides an isolated strength assessment of the quadriceps and hamstring muscles on an individual basis and typically uses a sophisticated testing machine having a mechanical strength-electronic measuring instrument in which force is exerted by the patient's foot against a lever-arm attached to a dynamometer and subsequently electronically measured while the patient remains sitting on the machine. Unfortunately, the isokinetic test does not assess balance or coordination and does not assess the entire lower extremity as one functional unit. Additionally, the isokinetic test is capital intensive for the rehabilitative administrating facility because the test typically requires the use of mechanical strength-electronic measuring instrumentation that is not only expensive but also sophisticated, thus requiring costly and time consuming training. Furthermore, the isokinetic test may also be cost intensive to the patient as charges related to the use of the mechanical strength-electronic measuring instrument are unfortunately not always reimbursed by insurance companies. With the advent of the managed care environment, isokinetic testing is not always clinically practical.

At the present time, there is no satisfactory test to assess muscle strength, balance, endurance, coordination and lower extremity function during rehabilitation of the lower extremity of the body that is also inexpensive and easy to administer on patients. As such, a need exists for other means of testing lower extremity function (e.g., the successful integration of strength, balance, endurance and coordination), and this test must be economical and easy for the clinician or healthcare professional to implement on patients. In particular, what is needed is a method and an apparatus for testing the lower extremity as one functional unit. Further needed is a method and an apparatus for testing the lower extremity that may be safely implemented during all stages of the rehabilitative process. More particularly, what is needed is a method and an apparatus for testing the lower extremity for an assessment of functional strength, balance, endurance and coordination of the entire lower extremity that is cost-effective and is simple to administer on patients.

SUMMARY OF THE INVENTION

The invention is a method and an apparatus for testing the entire lower extremity as one functional unit. More particularly, the invention is a method and an apparatus for testing the entire lower extremity for an assessment of functional strength, balance, endurance and coordination of the entire lower extremity. The invention may be safely implemented during all stages of the rehabilitative process. The invention is cost-effective and is simple to administer on patients.

The invented apparatus marks the maximum angle of movement at the hip, knee and ankle as the patient squats down using only a single test leg.

The invented lower extremity testing apparatus comprises a horizontally planar base having a knee tripodal portion and a hip tripodal portion adjustably coupled to the knee tripodal portion by a variable length connector, a knee post fixedly attached to the knee tripodal portion and vertically extending orthogonally away from the horizontal plane of the horizontally planar base, a hip post fixedly attached to the hip tripodal portion and vertically extending orthogonally away from the horizontal plane of the horizontally planar base, a knee bar that is adjustably connected to the knee post and a hip bar that is adjustably connected to the hip post. The knee tripodal portion may be releasably secured to the variable length connector by a locking fastener. The hip tripodal portion may be releasably secured to the variable length connector by a locking fastener. The knee bar may be releasably secured to the knee post by a locking fastener. The hip bar may be releasably secured to the hip post by a locking fastener.

In a preferred embodiment of the invention, the knee tripodal portion has a first central hollow pole having a diameter, a first lateral supporting pole fixedly attached to and extending perpendicularly away from the first central hollow pole, and a second lateral supporting pole fixedly attached to and extending perpendicularly away from the first central hollow pole to form a generally cross shape. The hip tripodal portion has a second central hollow pole having a diameter, a third lateral supporting pole fixedly attached to and extending perpendicularly away from the second central hollow pole, and a fourth lateral supporting pole fixedly attached perpendicularly to and extending perpendicularly away from the second central hollow pole to form a generally cross shape. The variable length connector is a cylindrical tube having a diameter that is less than the diameter of the first central hollow pole and the diameter of the second central hollow pole. The cylindrical tube of the variable length connector may be inserted and telescopically received within the first central hollow pole and the second central hollow pole to adjustably couple the first central hollow pole of the knee tripodal portion to the second central hollow pole of the hip tripodal portion. The first central hollow pole and the second central hollow pole may each be releasably secured to the cylindrical tube of the variable length connector by a locking fastener. The horizontally planar base, having the knee tripodal portion and the hip tripodal portion adjustably coupled to the knee tripodal portion by the variable length connector, is positioned along a horizontal plane of the floor and provides stability to the invented apparatus. The knee post is a hollow cylindrical tube having a diameter and fixedly attached to the first central hollow pole of the knee tripodal portion while extending vertically upward orthogonally away from the horizontal plane of the horizontally planar base. The knee bar has a diameter that is less than the diameter of the knee post. The knee bar may be inserted and telescopically received within the knee post to form a generally L shape. The knee bar may be releasably secured to the knee post by a locking fastener. The hip post is a hollow cylindrical tube having a diameter and fixedly attached to the second central hollow pole of the hip tripodal portion while extending vertically upward orthogonally away from the horizontal plane of the horizontally planar base. The hip bar has a diameter that is less than the diameter of the hip post. The hip bar may be inserted and telescopically received within the hip post to form a generally L shape. The hip bar may be releasably secured to the hip post by a locking fastener.

The variable length connector allows the invented apparatus to be horizontally adjusted by increasing or decreasing the distance between the knee tripodal portion and the hip tripodal portion depending upon a patient's particular physical dimension, such as the distance between the hip and the knee of the patient. The knee post and the hip post allows the invented apparatus to be adjusted in height by vertically extending or retracting the knee bar and the hip bar orthogonally away from or toward the horizontal plane of the horizontally planar base to accommodate a patient's particular physical dimension, such as the distance between the knee and the ankle of the patient. Adjustment of the distance between the knee tripodal portion and the hip tripodal portion, the height of the knee bar and the height of the hip bar during a trial single leg squat enables the clinician or healthcare professional to establish a desired and physically attainable degree of flexion (angle of bend or movement at a joint) to be achieved by the patient prior to undergoing lower extremity testing.

In operation, patients perform a trial single leg squat to a desired degree of flexion with each lower extremity to confirm an individual patient's ability to complete a single leg squat in a specified range-of-motion (ROM). Next, the patient is positioned proximally within the invented apparatus which is specifically adjusted to allow for the desired degree of flexion to be physically attained by the particular patient while performing single leg squats during lower extremity testing. The distance between the knee tripodal portion and the hip tripodal portion, the height of the knee bar and the height of the hip bar are adjusted such that at the desired degree of flexion to be achieved while performing single leg squats during lower extremity testing, the midline of the patella contacts the midline of the knee bar and the hip (ischial tuberosity) contacts the midline of the hip bar. This desired test position will be standardized for each individual subject based on the angle of ankle dorsiflexion achieved during the transition between eccentric and concentric phases of the single leg squat. A dorsiflexion angle of 20 degrees, as measured in a closed kinetic chain (CKC) is used to standardize the desired test position. Test angles are determined using standard goniometric measurement techniques at the ankle and knee joints. An inclinometer is attached to the lateral aspect of the test thigh to monitor the angle of flexion of the knee during warm-up, trial and test repetitions.

From the starting position with the test leg in full extension and the non-test leg flexed at the hip, knee and ankle, the patient squats down until the test knee lightly contacts the knee bar and the test hip (ischial tuberosity) lightly contacts the hip bar. Upon contact with the knee bar and the hip bar, the patient returns to the starting position. The patient's non-test knee and non-test hip are maintained in a flexed position to minimize hip substitution in the frontal and transverse planes of the body. During warm-up, trial and test repetitions, patients lightly contact the knee bar and the hip bar simultaneously to minimize biomechanical differences in squatting strategies. Furthermore, patients are not to "rest" or "unload" on the knee bar and the hip bar. One complete repetition is defined as successfully squatting from 0 degrees to the desired angle of flexion (i.e., 1° to 90°) of the knee joint and simultaneously contacting the knee bar and hip bar lightly, without touching or holding onto any object for balance or "resting" or "unloading" on the knee bar or the hip bar.

In a preferred embodiment, the patient performs five warm-up repetitions while touching or holding onto a stable object for balance, the patient then rests for thirty seconds, the patient then performs an additional five warm-up repetitions this time without touching or holding onto any object for balance, the patient then rests for one minute, next the patient performs a maximum number of repetitions as physically possible in 60 seconds without touching or holding onto any object for balance or "resting" or "unloading" on the knee bar or the hip bar, and then the patient may rest and subsequently repeat the aforementioned steps for the opposite leg.

OBJECTS OF THE INVENTION

The principal object of the invention is to provide a method and an apparatus for testing the entire lower extremity as one functional unit.

Another, more particular object of the invention is to provide a method and an apparatus for testing the entire lower extremity for an assessment of functional strength, balance, endurance and coordination of the entire lower extremity.

Another object of the invention is to provide a method and an apparatus for testing the entire lower extremity that may be safely implemented during all stages of the rehabilitative process.

Another object of the invention is to provide a method and an apparatus for testing the entire lower extremity that is cost-effective and is simple to administer on patients.

BRIEF DESCRIPTION OF THE DRAWINGS

These and other objects will become more fully understood by reference to the following detailed description of the invention and the appended drawing in which:

FIG. 3 is an isometric view of an alternative embodiment of a lower extremity testing apparatus in which the first lateral supporting pole and the second lateral supporting pole of the knee tripodal portion and the third lateral supporting pole and the fourth lateral supporting pole of the hip tripodal portion are each equipped with a stabilizer.

FIG. 4 is a front view of an alternative embodiment of a lower extremity testing apparatus shown in FIG. 3 in which a stabilizer is fully extended and in stabilizing contact with the floor during use of the lower extremity testing apparatus.

FIG. 5 is a side view of an alternative embodiment of a lower extremity testing apparatus shown in FIG. 3 in which the stabilizer is fully extended and in stabilizing contact with the floor during use of the lower extremity testing apparatus.

FIG. 6 is a side view of an alternative embodiment of a lower extremity testing apparatus shown in FIG. 3 in which the stabilizer is fully retracted during non-use or transportation of the lower extremity testing apparatus.

DETAILED DESCRIPTION OF THE INVENTION

The invention is a method and an apparatus for testing the entire lower extremity as one functional unit. More particularly, the invention is a method and an apparatus for testing the entire lower extremity for an assessment of functional strength, balance, endurance and coordination of the entire lower extremity. The invention may be safely implemented during all stages of the rehabilitative process. The invention is cost-effective and is simple to administer on patients.

Figure 1:
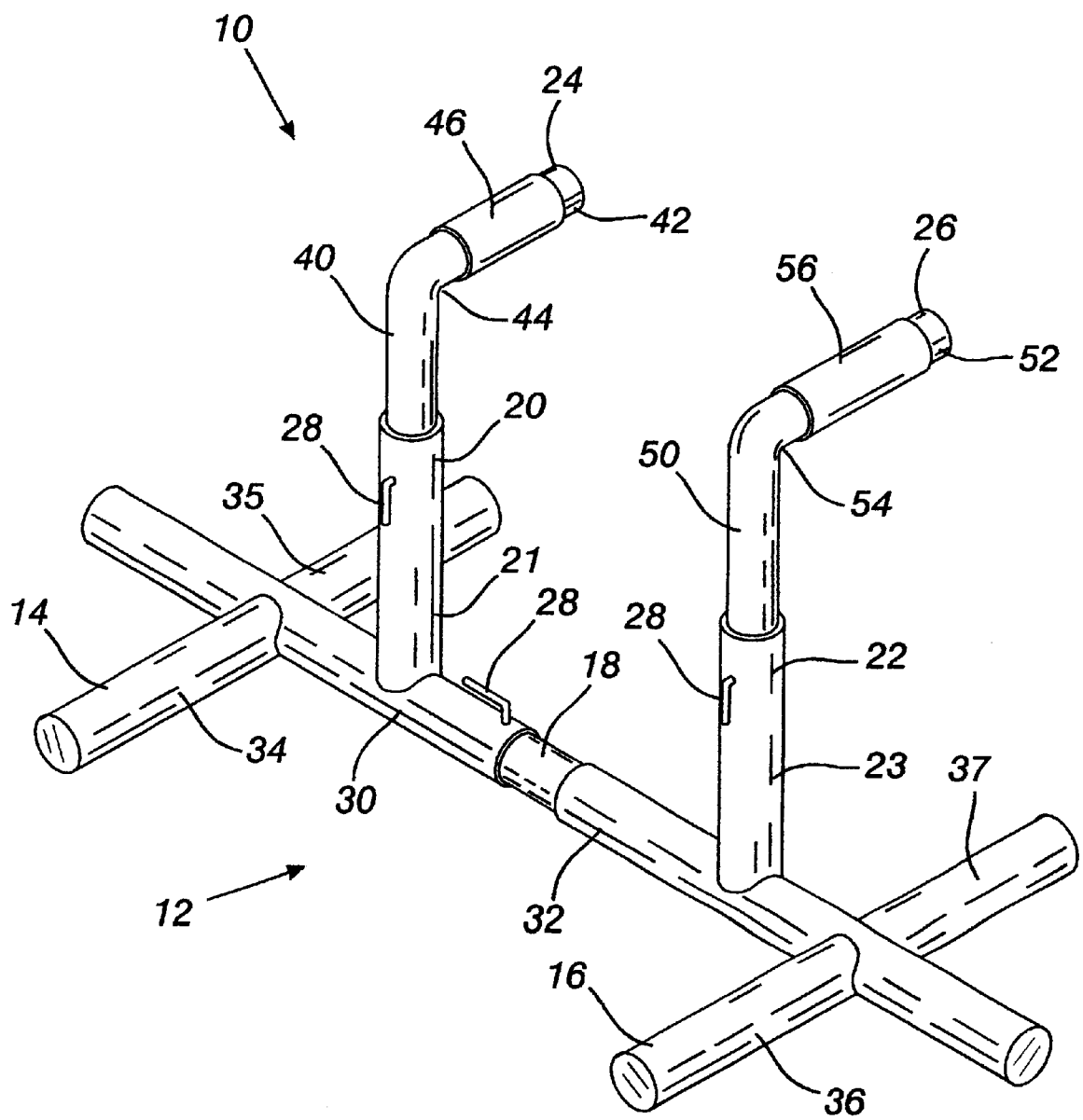
FIG. 1 is a perspective view of a preferred embodiment of a lower extremity testing apparatus in accordance with the present invention.

Referring now to the drawings, FIG. 1 is an isometric view of a lower extremity testing apparatus 10, that comprises a horizontally planar base 12 having a knee tripodal portion 14 and a hip tripodal portion 16 adjustably coupled to the knee tripodal portion 14 by a variable length connector 18, a knee post 20 fixedly attached to the knee tripodal portion 14 and vertically extending orthogonally away from the horizontal plane of the horizontally planar base 12, a hip post 22 fixedly attached to the hip tripodal portion 16 and vertically extending orthogonally away from the horizontal plane of the horizontally planar base 12, a knee bar 24 that is adjustably connected to the knee post 20 and a hip bar 26 that is adjustably connected to the hip post 22. The knee tripodal portion 14 may be releasably secured to the variable length connector 18 by a locking fastener 28. The hip tripodal portion 16 may be releasably secured to the variable length connector 18 by a locking fastener 28. The knee bar 24 may be releasably secured to the knee post 20 by a locking fastener 28. The hip bar 26 may be releasably secured to the hip post 22 by a locking fastener 28.

The knee tripodal portion 14 has a first central hollow pole 30 having a diameter and positioned along the horizontal plane of the horizontally planar base 12, a first lateral supporting pole 34 positioned along the horizontal plane of the horizontally planar base 12 fixedly attached to the first central hollow pole 30 and extending perpendicularly away from the first central hollow pole 30, and a second lateral supporting pole 35 positioned along the horizontal plane of the horizontally planar base 12 fixedly attached to the first central hollow pole 30 and extending perpendicularly away from the first central hollow pole 30 to form a generally cross shape.

The hip tripodal portion 16 has a second central hollow pole 32 having a diameter and positioned along the horizontal plane of the horizontally planar base 12, a third lateral supporting pole 36 positioned along the horizontal plane of the horizontally planar base 12 fixedly attached to the second central hollow pole 32 and extending perpendicularly away from the second central hollow pole 32, and a fourth lateral supporting pole 37 positioned along the horizontal plane of the horizontally planar base 12 fixedly attached to the second central hollow pole 32 and extending perpendicularly away from the second central hollow pole 32 to form a generally cross shape.

The variable length connector 18 is a cylindrical tube having a diameter that is less than the diameter of the first central hollow pole 30 and the diameter of the second central hollow pole 32. The cylindrical tube of the variable length connector 18 may be inserted and telescopically received within the first central hollow pole 30 and the second central hollow pole 32 to adjustably couple the first central hollow pole 30 of the knee tripodal portion 14 to the second central hollow pole 32 of the hip tripodal portion 16. The first central hollow pole 30 and the second central hollow pole 32 may each be releasably secured to the cylindrical tube of the variable length connector 18 by a locking fastener 28. The horizontally planar base 12, having the knee tripodal portion 14 and the hip tripodal portion 16 adjustably coupled to the knee tripodal portion 14 by the variable length connector 18, is positioned along a horizontal plane of the floor and provides stability to the invented apparatus 10.

The knee post 20 is a first hollow cylindrical tube 21 having a diameter and fixedly attached to the first central hollow pole 30 of the knee tripodal portion 14 while extending vertically upward orthogonally away from the horizontal plane of the horizontally planar base 12. The knee bar 24 has a diameter that is less than the diameter of the first hollow cylindrical tube 21 of the knee post 20. The knee bar 24 may be inserted and telescopically received within the first hollow cylindrical tube 21 of the knee post 20 to form a generally L shape. The knee bar 24 may be releasably secured to the knee post 20 by a locking fastener 28.

The hip post 22 is a second hollow cylindrical tube 23 having a diameter and fixedly attached to the second central hollow pole 32 of the hip tripodal portion 16 while extending vertically upward orthogonally away from the horizontal plane of the horizontally planar base 12. The hip bar 26 has a diameter that is less than the diameter of the second hollow cylindrical tube 23 of the hip post 22. The hip bar 26 may be inserted and telescopically received within the second hollow cylindrical tube 23 of the hip post 22 to form a generally L shape. The hip bar 26 may each be releasably secured to the hip post 22 by a locking fastener 28.

The knee bar 24 has a first vertical segment 40 and a first horizontal segment 42 that is interconnected to the first vertical segment 40 by a first elbow bend 44. The first vertical segment 40 has a diameter that is less than the diameter of the first hollow cylindrical tube 21 of the knee post 20. The first vertical segment 40 may be inserted and telescopically received within the first hollow cylindrical tube 21 of the knee post 20. The first vertical segment 40 of the knee bar 24 may also have stippling or markings on the exterior surface for indication of the relative height for positioning the knee bar 24. The first vertical segment 40 of the knee bar 24 may be releasably secured to the knee post 20 by a locking fastener 28. The first horizontal segment 42 may have a substantially hollow cylindrical knee cushion 46 attached to the exterior of the knee bar 24. The substantially hollow cylindrical knee cushion 46 provides the knee bar 24 with a soft surface to protect the patient's knee when it contacts the knee bar 24 while performing single leg squats.

The hip bar 26 has a second vertical segment 50 and a second horizontal segment 52 that is interconnected to the second vertical segment 50 by a second elbow bend 54. The second vertical segment 50 has a diameter that is less than the diameter of the second hollow cylindrical tube 23 of the hip post 22. The second vertical segment 50 may be inserted and telescopically received within the second hollow cylindrical tube 23 of the hip post 22. The second vertical segment 50 of the hip bar 26 may also have stippling or markings on the exterior surface for indication of the relative height for positioning the hip bar 26. The second vertical segment 50 of the hip bar 26 may be releasably secured to the hip post 22 by a locking fastener 28. The second horizontal segment 52 may have a substantially hollow cylindrical hip cushion 56 attached to the exterior of the hip bar 26. The substantially hollow cylindrical hip cushion 56 provides the hip bar 26 with a soft surface to protect the patient's hip when it contacts the hip bar 26 while performing single leg squats.

The variable length connector 18 allows the invented apparatus 10 to be horizontally adjusted by increasing or decreasing the distance between the knee tripodal portion 14 and the hip tripodal portion 16 depending upon a patient's particular physical dimension, such as the distance between the hip and the knee of the patient. The variable length connector 18 may also have stippling or markings on the exterior surface for indication of the relative distance or positioning of the knee tripodal portion 14 and the hip tripodal portion 16. The knee post 20 and the hip post 22 allows the invented apparatus 10 to be adjusted in height by vertically extending or retracting the knee bar 24 and the hip bar 26 orthogonally away from or toward the horizontal plane of the horizontally planar base 12 to accommodate a patient's particular physical dimension, such as the distance between the knee and the ankle of the patient. Adjustment of the distance between the knee tripodal portion 14 and the hip tripodal portion 16, the height of the knee bar 24 and the height of the hip bar 26 during a trial single leg squat enables the clinician or healthcare professional to establish a desired and physically attainable degree of flexion to be achieved by the patient prior to undergoing lower extremity testing.

A clinician or healthcare professional can accommodate a specific patient's particular physical dimension, such as the distance between the hip and the knee of the patient, by increasing or decreasing the distance between the knee tripodal portion 14 and the hip tripodal portion 16. Once the distance between the knee tripodal portion 14 and the hip tripodal portion 16 is selected for a specific patient, a locking fastener 28 is utilized to releasably secure the knee tripodal portion 14 and the hip tripodal portion 16 to the variable length connector 18 thus stabilizing the horizontally planar base 12 for lower extremity testing.

A clinician or healthcare professional can accommodate a specific patient's particular physical dimension, such as the distance between the knee and the ankle of the patient, by vertically extending or retracting the knee bar 24 and the hip bar 26 orthogonally away from or toward the horizontal plane of the horizontally planar base 12. More specifically, the clinician or healthcare professional can adjust the height of the first horizontal segment 42 of the knee bar 24 by vertically extending or retracting the first vertical segment 40 of the knee bar 24, which is inserted and telescopically received within the knee post 20 of the knee tripodal portion 14, orthogonally away from or toward the horizontal plane of the horizontally planar base 12. The clinician or healthcare professional can also adjust the height of the second horizontal segment 52 of the hip bar 26 by vertically extending or retracting the second vertical segment 50 of the hip bar 26, which is inserted and telescopically received within the hip post 22 of the hip tripodal portion 16, orthogonally away from or toward the horizontal plane of the horizontally planar base 12. Once the desired height of the first horizontal segment 42 of the knee bar 24 is obtained, the clinician or healthcare professional can then insert a locking fastener 28 into the first vertical segment 40 of the knee bar 24 to releasably secure the desired height of the first horizontal segment 42 for the duration of the lower extremity testing. Once the desired height of the second horizontal segment 52 of the hip bar 26 is obtained, the clinician or healthcare professional can then insert a locking fastener 28 into the second vertical segment 50 of the hip bar 26 to releasably secure the desired height of the second horizontal segment 52 for the duration of the lower extremity testing. All positions will be recorded for future testing references.

The invented apparatus 10 marks the maximum angle of movement at the hip, knee and ankle as the patient squats down using only a single test leg. In operation, patients perform a trial single leg squat to a desired degree of flexion with each lower extremity to confirm an individual patient's ability to complete a single leg squat in a specified range-of-motion (ROM). Next, the patient is positioned proximally within the invented apparatus 10 which is specifically adjusted to allow for the desired degree of hip, knee and ankle flexion to be physically attained by the particular patient while performing single leg squats during lower extremity testing. The distance between the knee tripodal portion 14 and the hip tripodal portion 16, the height of the knee bar 24 and the height of the hip bar 26 are adjusted such that at the desired degree of hip, knee and ankle flexion to be achieved while performing single leg squats during lower extremity testing, the midline of the patella contacts the midline of the knee bar 24 and the hip (ischial tuberosity) contacts the midline of the hip bar 26. This desired test position will be standardized for each individual subject based on the angle of ankle dorsiflexion achieved during the transition between eccentric and concentric phases of the single leg squat. A dorsiflexion angle of 20 degrees, as measured in a closed kinetic chain (CKC) is used to standardize the desired test position. Test angles are determined using standard goniometric measurement techniques at the ankle and knee joints. An inclinometer is attached to the lateral aspect of the test thigh to monitor the angle of flexion of the knee during warn-up, trial and test repetitions.

From the starting position with the test leg in fill extension and the non-test leg flexed at the hip, knee and ankle, the patient squats down until the test knee lightly contacts the knee bar 24 and the test hip (ischial tuberosity) lightly contacts the hip bar 26. Upon contact with the knee bar 24 and the hip bar 26, the patient returns to the starting position.

The patient's non-test knee and non-test hip are maintained in a flexed position to minimize hip substitution in the frontal and transverse planes of the body. During warm-up, trial and test repetitions, patients lightly contact the knee bar 24 and the hip bar 26 simultaneously to minimize biomechanical differences in squatting strategies. Furthermore, patients are not to "rest" or "unload" on the knee bar 24 and the hip bar 26. One complete repetition is defined as successfully squatting from 0 degrees to the desired angle of flexion (i.e., 1° to 90°) of the knee joint and simultaneously contacting the knee bar 24 and hip bar 26 lightly without touching or holding onto any object for balance or "resting" or "unloading" on the knee bar 24 or the hip bar 26.

In a preferred embodiment, the patient performs five warm-up repetitions while touching or holding onto a stable object for balance, the patient then rests for thirty seconds, the patient then performs an additional five warm-up repetitions this time without touching or holding onto any object for balance, the patient then rests for one minute, next the patient performs a maximum number of repetitions as physically possible in 60 seconds without touching or holding onto any object for balance or "resting" or "unloading" on the knee bar 24 or the hip bar 26, and then the patient may rest and subsequently repeat the aforementioned steps for the opposite leg.

ALTERNATIVE EMBODIMENTS

Alternatively, any or all of the elements of the invention that are temporarily coupled, attached, connected or secured together by a variable, releasable, adjustable or locking means may be permanently "fixed" together by any convenient means such as glueing, welding, riveting, bolting, screwing or pinning.

Figure 2:
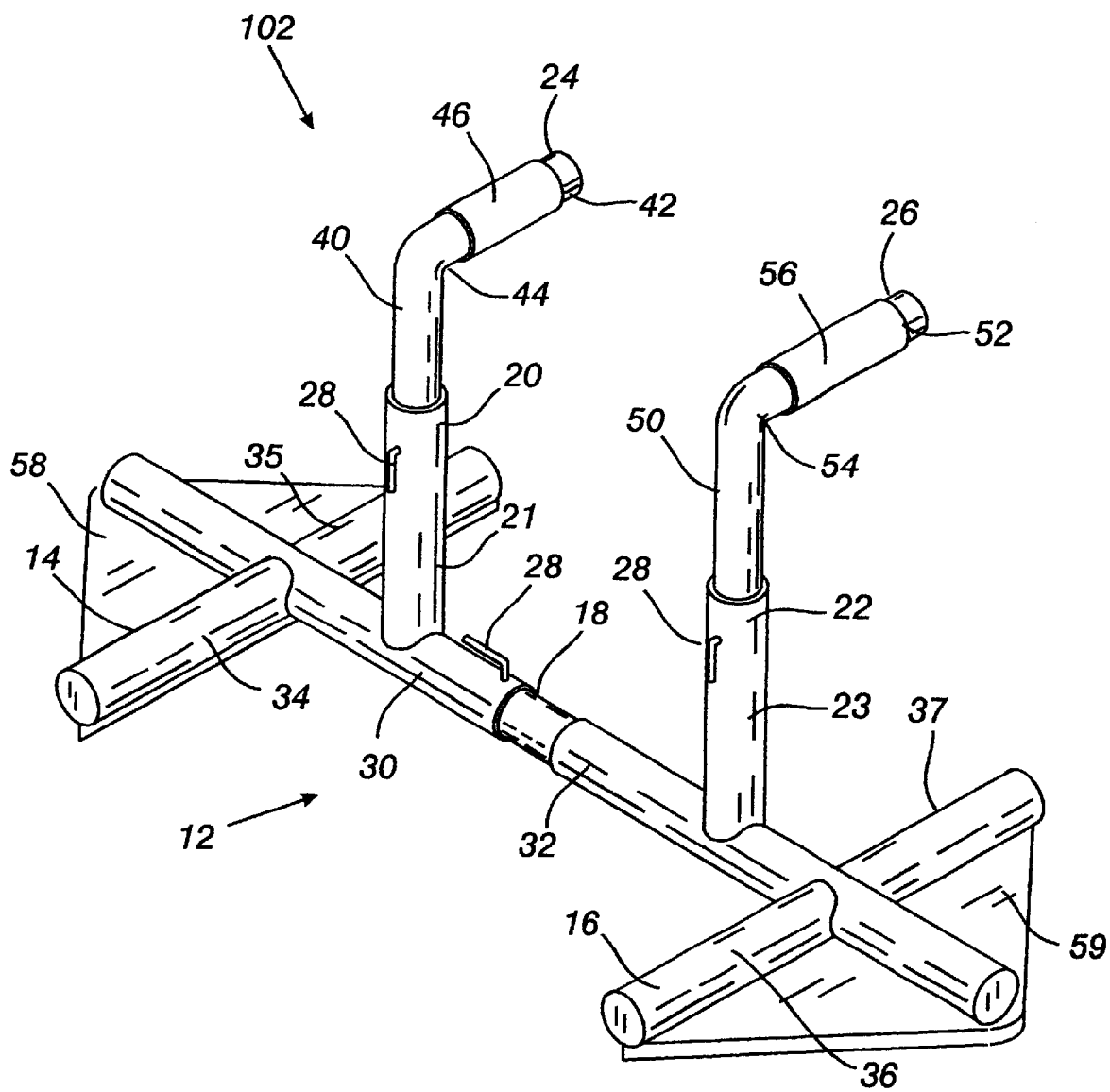
FIG. 2 is an isometric view of an alternative embodiment of a lower extremity testing apparatus in which the knee tripodal portion is connected to, or mounted on, a flat triangular knee tripodal portion support plate and the hip tripodal portion is connected to, or mounted on, a flat triangular hip tripodal portion support plate.

FIG. 2 is an isometric view of an alternative embodiment of a lower extremity testing apparatus 102 in which the knee tripodal portion 14 is connected to, or mounted on, a flat triangular knee tripodal portion support plate 58 and the hip tripodal portion 16 is connected to, or mounted on, a flat triangular hip tripodal portion support plate 59. An alternative embodiment of a lower extremity testing apparatus can be envisioned in which the flat triangular knee tripodal portion support plate 58 is a pad and the flat triangular hip tripodal portion support plate 59 is a pad.

FIG. 3 is an isometric view of an alternative embodiment of a lower extremity testing apparatus 104 in which the first lateral supporting pole 34 and the second lateral supporting pole 35 of the knee tripodal portion 14 and the third lateral supporting pole 36 and the fourth lateral 11 supporting pole 37 of the hip tripodal portion 16 are each equipped with a stabilizer 60. The stabilizer 60 includes a locking hinge 62 mounted to a respective lateral supporting pole 34, 35, 36, 37, a shaft 64 having a first end 66 hingedly connected to the locking hinge 62 and a second end 68 opposing the first end 66, and a footplate 70 fixedly attached to the second end 68 of the shaft 64. FIG. 4 is a front view of an alternative embodiment of a lower extremity testing apparatus shown in FIG. 3 in which a stabilizer 60 is fully extended and in stabilizing contact with the floor during use of the lower extremity testing apparatus 104. FIG. 5 is a side view of an alternative embodiment of a lower extremity testing apparatus 104 shown in FIG. 3 in which the stabilizer 60 is fully extended and in stabilizing contact with the floor during use of the lower extremity testing apparatus 104. FIG. 6 is a side view of an alternative embodiment of a lower extremity testing apparatus 104 shown in FIG. 3 in which the stabilizer 60 is fully retracted during non-use or transportation of the lower extremity testing apparatus 104.

Figure 7:
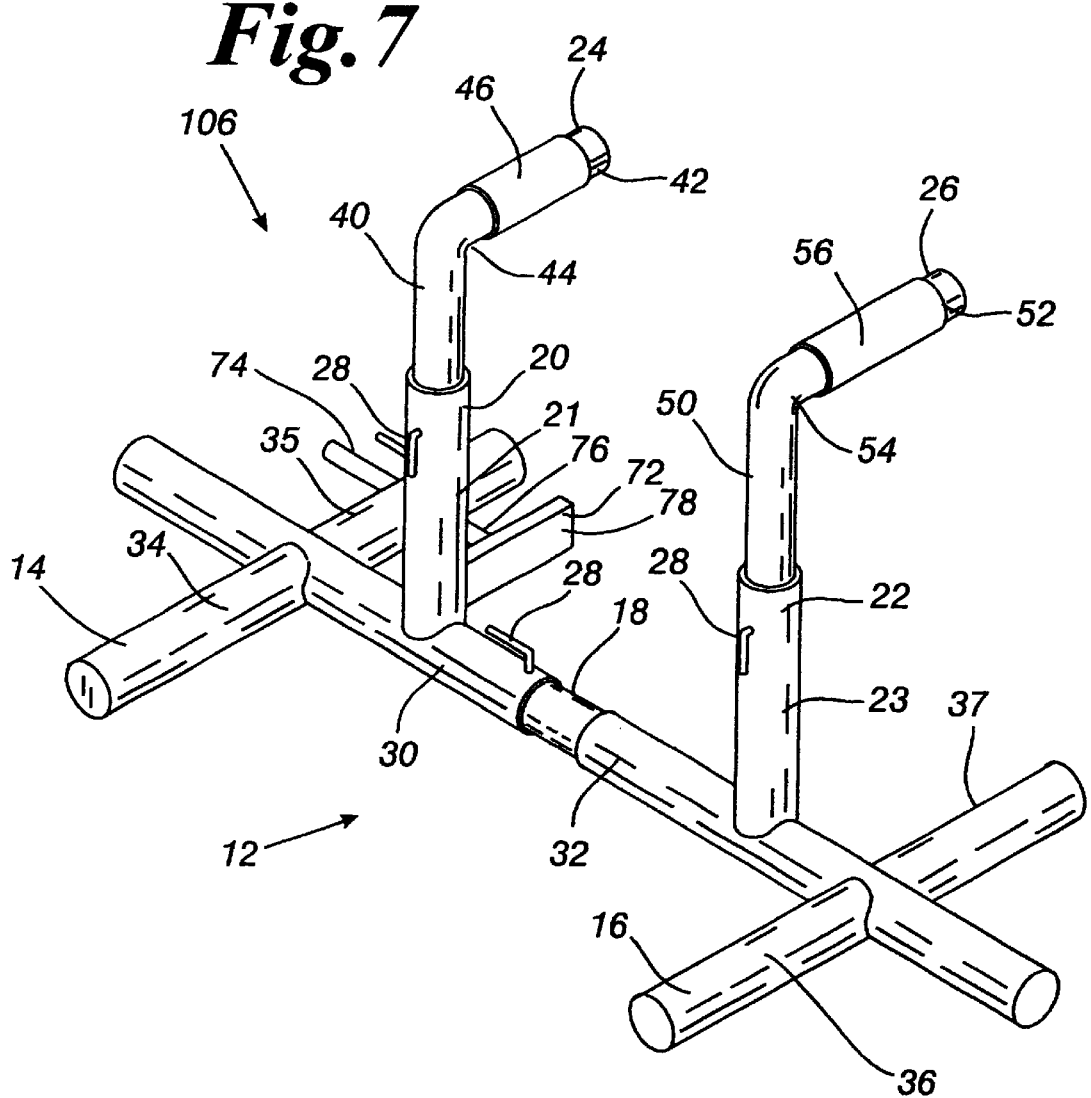
FIG. 7 is an isometric view of an alternative embodiment of a lower extremity testing apparatus in which the second lateral supporting pole of the knee tripodal portion is equipped with a foot placement guide.
Figure 8:
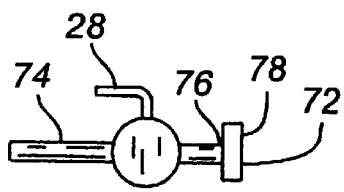
FIG. 8 is a side view of an alternative embodiment of a lower extremity testing apparatus shown in FIG. 7 in which the foot placement guide is extended for positioning the particular patient's foot a specific distance away from the second lateral supporting pole of the knee tripodal portion.
Figure 9:
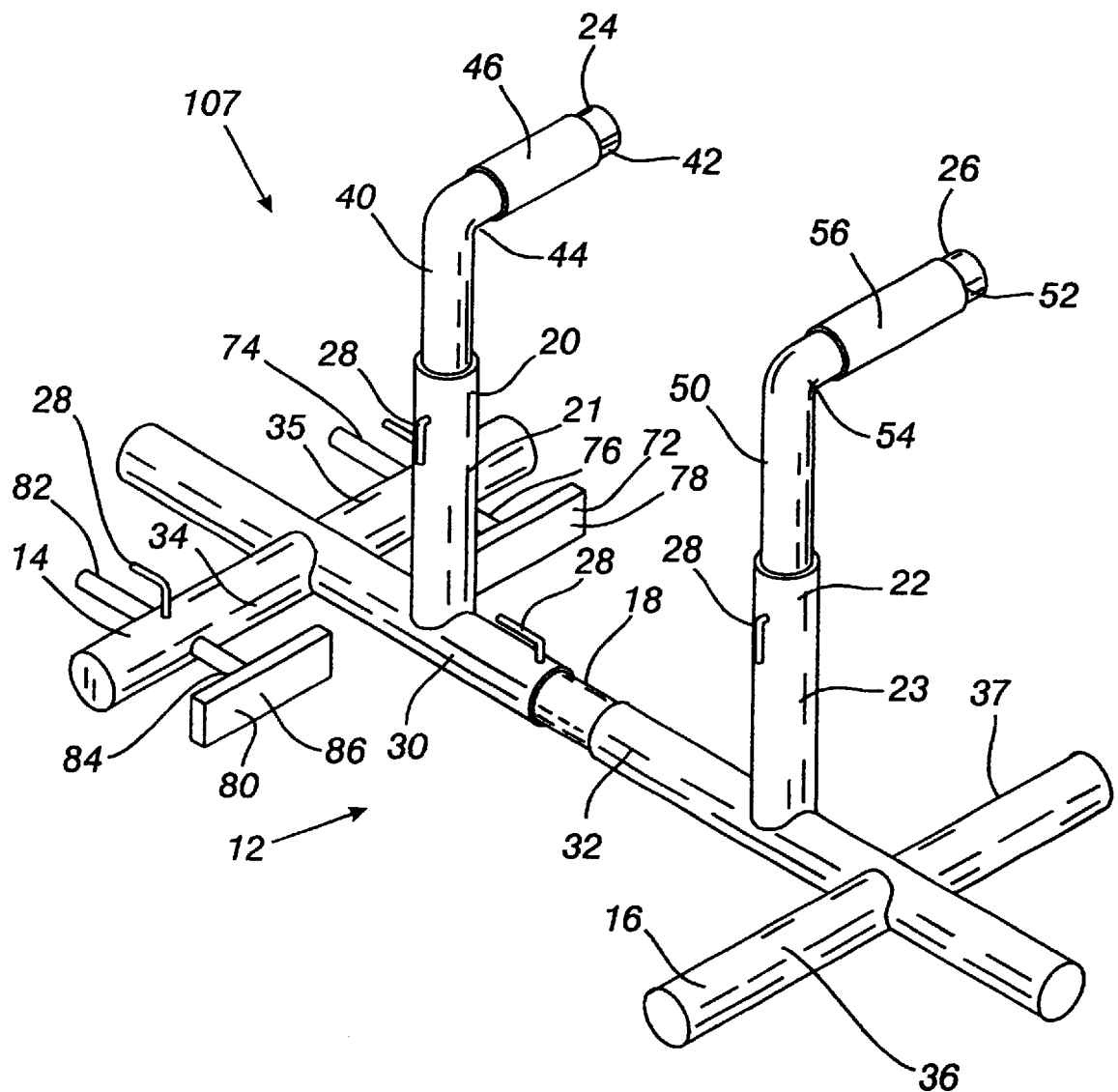
FIG. 9 is an isometric view of an alternative embodiment of the alternative embodiment of a lower extremity testing apparatus shown in FIG. 7 in which the first lateral supporting pole and the second lateral supporting pole of the knee tripodal portion are each equipped with a respective foot placement guide.

FIG. 7 is an isometric view of an alternative embodiment of a lower extremity testing apparatus 106 in which the second lateral supporting pole 35 of the knee tripodal portion 14 is equipped with a second foot placement guide 72. The second foot placement guide 72 includes a second rod 74 that perpendicularly transverses through the second lateral supporting pole 35 of the knee tripodal portion 14 along the horizontal plane of the horizontally planar base 12, a second end 76 that extends toward the fourth lateral supporting pole 37 of the hip tripodal portion 16, and a second solid plate 78 secured to the second end 76 of the second rod 74. The second rod 74 may also have stippling or markings on the exterior surface for indication of the relative lengths for positioning the particular patient's foot a specific distance away from the second lateral supporting pole 35 of the knee tripodal portion 14 and toward the fourth lateral supporting pole 37 of the hip tripodal portion 16. FIG. 8 is a side view of an alternative embodiment of a lower extremity testing apparatus 106 shown in FIG. 7 in which the second foot placement guide 72 is extended for positioning the particular patient's foot a specific distance away from the second lateral supporting pole 35 of the knee tripodal portion 14. FIG. 9 is an isometric view of an alternative embodiment 107 of the alternative embodiment of the lower extremity testing apparatus 106 shown in FIG. 7 in which the second lateral supporting pole 35 of the knee tripodal portion 14 is equipped with a second foot placement guide 72, as described above, and the first lateral supporting pole 34 of the knee tripodal portion 14 is equipped with a first foot placement guide 80. The first foot placement guide 80 includes a first rod 82 that perpendicularly transverses through the first lateral supporting pole 34 of the knee tripodal portion 14 along the horizontal plane of the horizontally planar base 12, a first end 84 that extends toward the third lateral supporting pole 36 of the hip tripodal portion 16, and a first solid plate 86 secured to the first end 84 of the first rod 82.

A clinician or healthcare professional can position the particular patient's foot a specific distance away from the second lateral supporting pole 35 of the knee tripodal portion 14 and toward the fourth lateral supporting pole 37 of the hip tripodal portion 16 by horizontally extending or retracting the second solid plate 78 secured to the second end 76 of the second rod 74 perpendicularly away from the second lateral supporting pole 35 of the knee tripodal portion 14 and toward the fourth lateral supporting pole 37 of the hip tripodal portion 16 along the horizontal plane of the horizontally planar base 12. Once the desired position of the particular patient's foot is obtained, the clinician or healthcare professional can then insert a locking fastener 28 into the second lateral supporting pole 35 to releasably secure the desired position of the particular patient's foot for the duration of the lower extremity testing.

A clinician or healthcare professional can position the particular patient's foot a specific distance away from the first lateral supporting pole 34 of the knee tripodal portion 14 and toward the third lateral supporting pole 36 of the hip tripodal portion 16 by horizontally extending or retracting the first solid plate 86 secured to the first end 84 of the first rod 82 perpendicularly away from the first lateral supporting pole 34 of the knee tripodal portion 14 and toward the third lateral supporting pole 36 of the hip tripodal portion 16 along the horizontal plane of the horizontally planar base 12. Once the desired position of the particular patient's foot is obtained, the clinician or healthcare professional can then insert a locking fastener 28 into the first lateral supporting pole 34 to releasably secure the desired position of the particular patient's foot for the duration of the lower extremity testing.

Figure 10:
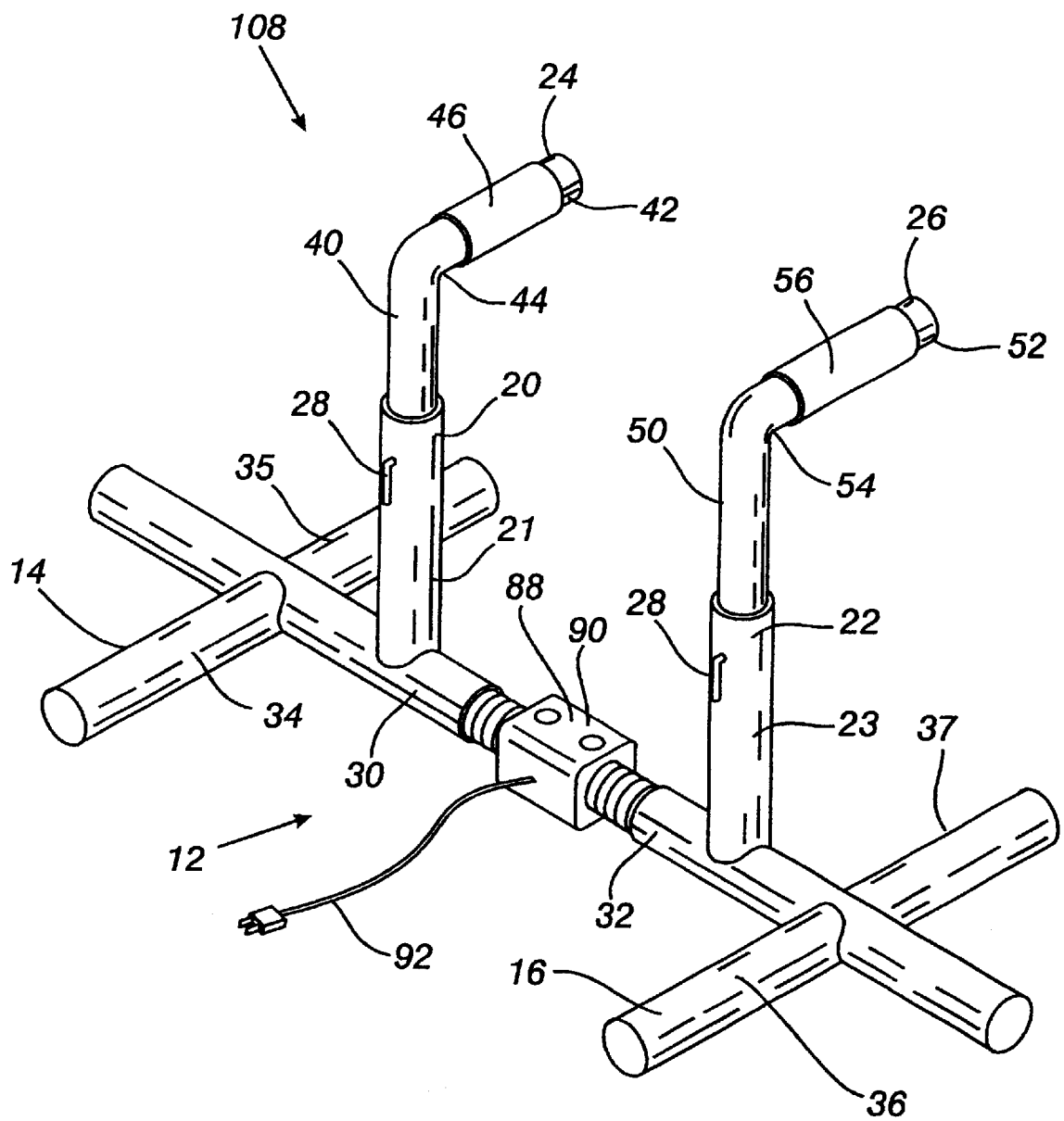
FIG. 10 is an isometric view of an alternative embodiment of a lower extremity testing apparatus in which the variable length connector, that adjustably couples the knee tripodal portion to the hip tripodal portion, may be horizontally adjusted by a mechanical, hydraulic or electrical mechanism (i.e., motor, air or liquid fluid, or digital).

FIG. 10 is an isometric view of an alternative embodiment of a lower extremity testing apparatus 108 in which the variable length connector 18, that adjustably couples the knee tripodal portion 14 to the hip tripodal portion 16, may be horizontally adjusted by a mechanical, hydraulic or electrical (i.e., motor, air or liquid fluid, or digital) adjustment mechanism 88, instead of manually adjusted. In addition, the horizontally adjusted variable length connector 18 may be equipped with a built-in mechanical, hydraulic or electrical braking device 90, instead of a manually inserted locking fastener 28, to releasably secure the desired distance between the knee tripodal portion 14 and the hip tripodal portion 16 for the duration of the lower extremity testing. The mechanical, hydraulic or electrical (i.e., motor, air or liquid fluid, or digital) adjustment mechanism 88 and the mechanical, hydraulic or electrical braking device 90 may be equipped with a power supply cord 92.

Figure 11:
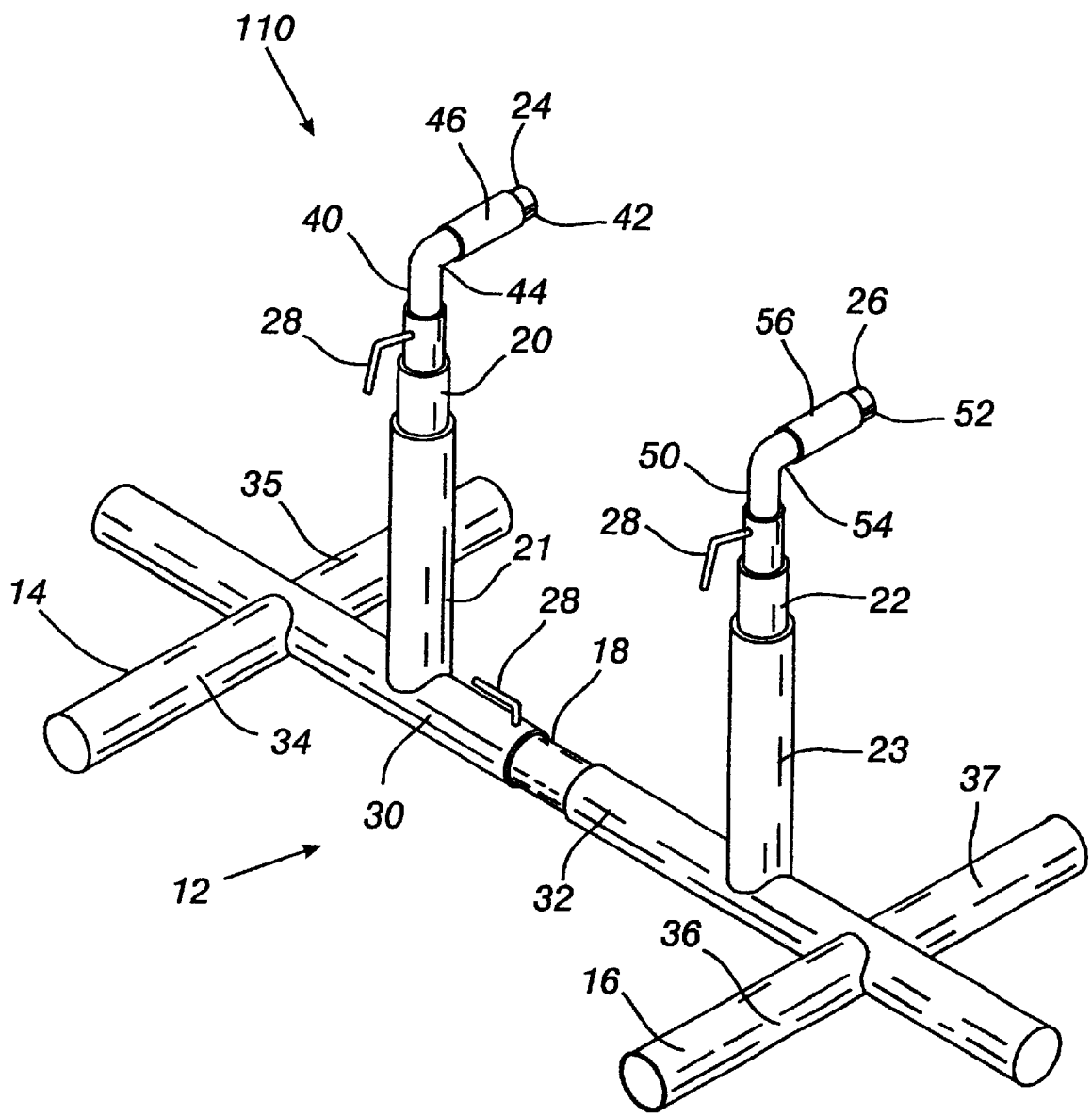
FIG. 11 is an isometric view of an alternative embodiment of a lower extremity testing apparatus in which the knee post 20 and the hip post 22 are made of multilevel telescopic construction and may be vertically adjusted by a manual, mechanical, hydraulic or electrical mechanism (i.e., locking fastener, motor, air or liquid fluid, or digital).

FIG. 11 is an isometric view of an alternative embodiment of a lower extremity testing apparatus 110 in which the knee post 20 and the hip post 22 are made of multilevel telescopic construction. The knee post 20 is fixedly attached to the knee tripodal portion 14 of the horizontally planar base 12. The knee post 20 vertically extends or retracts orthogonally away from or toward the horizontal plane of the horizontally planar base 12 via extension or retraction of the multilevel telescopic construction away from or toward the horizontal plane of the horizontally planar base 12, respectively. The knee bar 24 is adjustably connected to the uppermost multilevel telescopic construction of the knee post 20. The hip post 22 is fixedly attached to the hip tripodal portion 16 of the horizontally planar base 12. The hip post 20 vertically extends or retracts orthogonally away from or toward the horizontal plane of the horizontally planar base 12 via extension or retraction of the multilevel telescopic construction away from or toward the horizontal plane of the horizontally planar base 12, respectively. The hip bar 26 is adjustably connected to the uppermost multilevel telescopic construction of the hip post 22. The vertical adjustment of the multilevel telescopic construction of the knee post 20 and the hip post 22 may be accomplished by a manual adjustment means, such as insertion of a locking fastener 28 (shown) or a mechanical, hydraulic or electrical (i.e., motor, air or liquid fluid, or digital) adjustment mechanism 88 (not shown). In addition, the vertically adjusted multilevel telescopic construction of the knee post 20 and the hip post 22 may each be equipped with a manually inserted locking fastener 28 (shown) or a mechanical, hydraulic or electrical (i.e., motor, air or liquid fluid, or digital) braking device 90 (not shown) to releasably secure the desired vertical distance between the knee tripodal portion 14 and the knee bar 24 as well as the desired vertical distance between the hip tripodal portion 16 and the hip bar 26, for the duration of the lower extremity testing.

Figure 12:
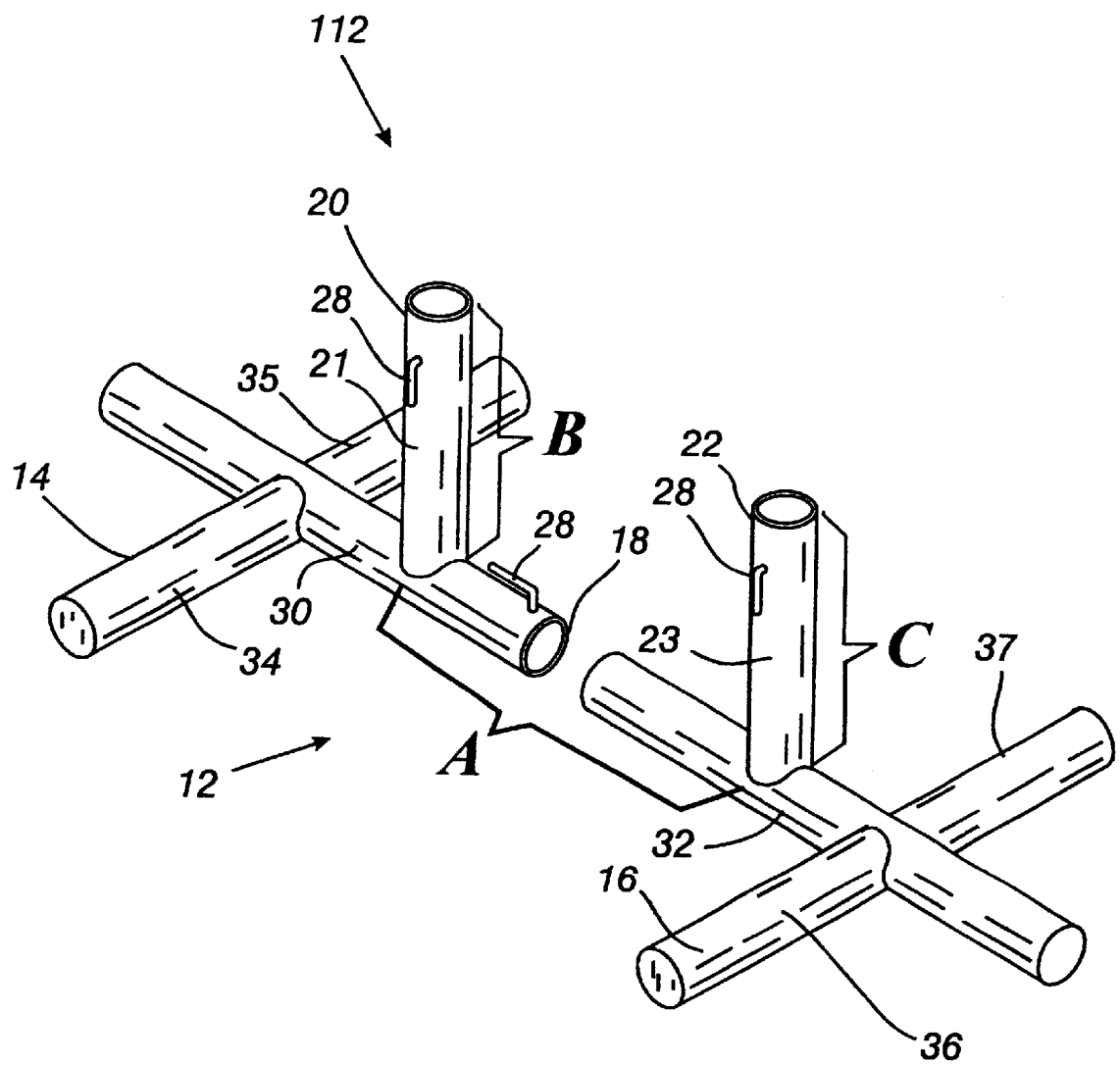
FIG. 12 is an isometric view of an alternative embodiment of a lower extremity testing apparatus illustrating which sections (designated by "A", "B" and "C") of the lower extremity testing apparatus must be of hollow construction and the remainder sections that may be of either hollow or solid construction.

FIG. 12 is an isometric view of an alternative embodiment of a lower extremity testing apparatus 112 illustrating which sections (designated by "A", "B" and "C") of the lower extremity testing apparatus 112 must be of hollow construction and the remainder sections that may be of either hollow or solid construction. The first central hollow pole 30 of the knee tripodal portion 14 and the second central hollow pole 32 of the hip tripodal portion 16 may be either hollow or solid, except for section "A" (designated in FIG. 12) which must be hollow so as to enable the pole of the variable length connector 18 to be inserted within a section "A" of the first central hollow pole 30 and a section "A" of the second central hollow pole 32 to telescopically couple the knee tripodal portion 14 to the hip tripodal portion 16. Knee post 20 of the knee tripodal portion 14 must be hollow (designated as "B" in FIG. 11) so as to enable the first vertical segment 40 of the knee bar 24 to be telescopically received within the knee post 20. Hip post 22 of the hip tripodal portion 16 must be hollow (designated as "C" in FIG. 11) so as to enable the second vertical segment 50 of the hip bar 26 to be telescopically received within the hip post 22. The first lateral supporting pole 34 and the second lateral supporting pole 35 of the knee tripodal portion 14 and the third lateral supporting pole 36 and the fourth lateral supporting pole 37 of the hip tripodal portion 16 may be either hollow or solid. The variable length connector 18, knee bar 24 and hip bar 26 may be either hollow or solid.

Figure 13:
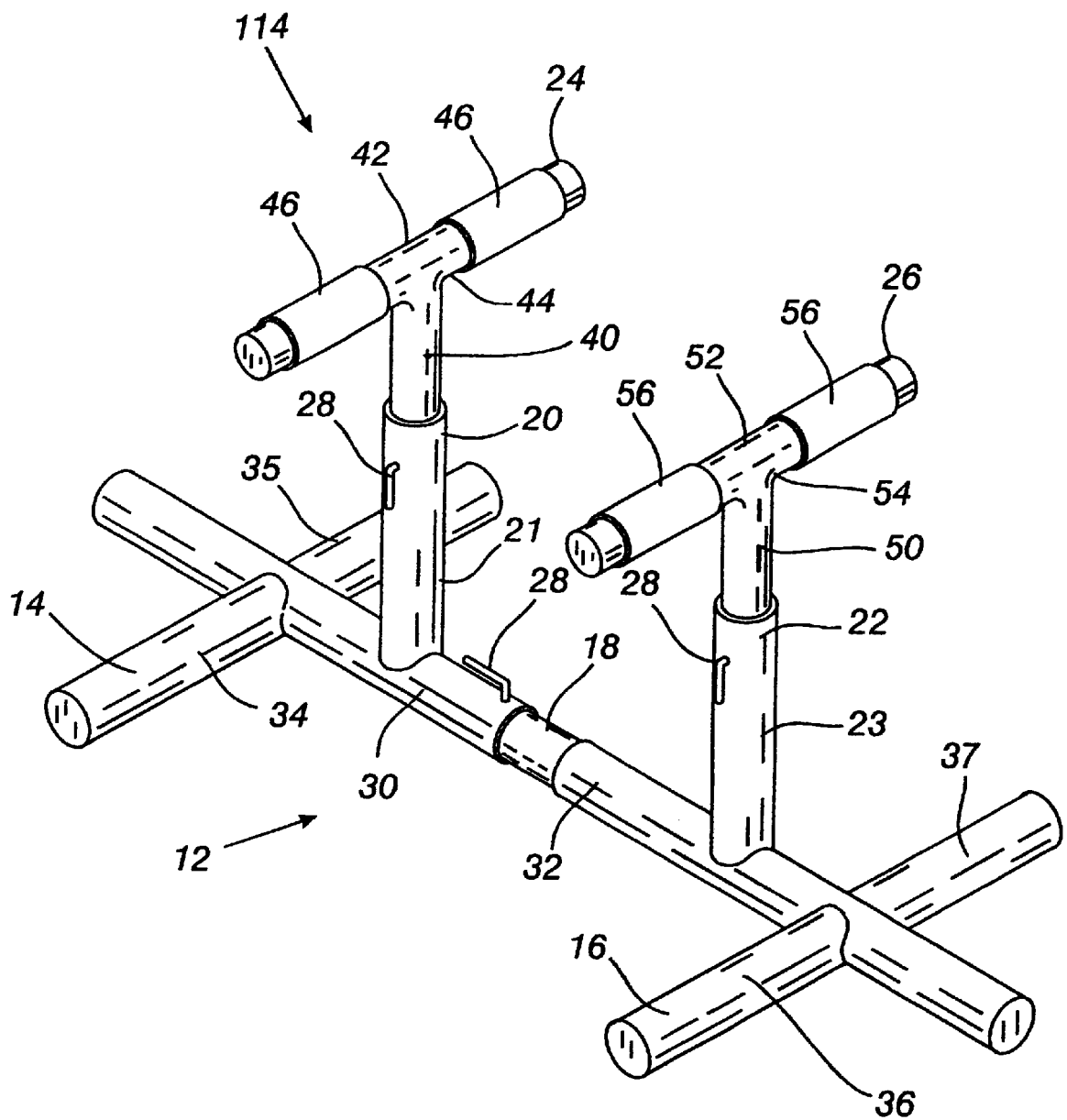
FIG. 13 is an isometric view of an alternative embodiment of a lower extremity testing apparatus in which the first vertical segment of the knee bar intersects the first horizontal segment of the knee bar to form a generally T shape and the second vertical segment of the hip bar intersects the second horizontal segment of the hip bar to form a generally T shape.

FIG. 13 is an isometric view of an alternative embodiment of a lower extremity testing apparatus 114 in which the first vertical segment 40 of the knee bar 24 intersects the midpoint of the first horizontal segment 42 of the knee bar 24 to form a generally T shape and the second vertical segment 50 of the hip bar 26 intersects the midpoint of the second horizontal segment 52 of the hip bar 26 to form a generally T shape. An alternative embodiment of a lower extremity testing apparatus can be envisioned in which the T shaped knee bar 24 and the T shaped hip bar 26 are used in conjunction with the knee post 20 and the hip post 22 of the alternative embodiment shown in FIG. 11, which are made of multilevel telescopic construction.

SUMMARY OF THE ACHIEVEMENT OF THE OBJECTS OF THE INVENTION

It is readily apparent that I have invented a method and an apparatus for testing the entire lower extremity as one functional unit. The present invention provides a method and an apparatus for testing the entire lower extremity for an assessment of functional strength, balance, endurance and coordination of the entire lower extremity. The present invention provides a method and an apparatus for testing the entire lower extremity that may be safely implemented during all stages of the rehabilitative process. The present invention provides a method and an apparatus for testing the entire lower extremity that is cost-effective and is simple to administer on patients.

It is to be understood that the foregoing description and specific embodiments are merely illustrative of the best mode of the invention and the principles thereof, and that various modifications and additions may be made to the apparatus by those skilled in the art, without departing from the spirit and scope of this invention.

What is claimed is:

1. An apparatus for testing the entire lower extremity function of a human body, the apparatus comprising:
   a horizontally planar base, comprising:
      a knee tripodal portion;
      a hip tripodal portion; and
      a connector coupling said knee tripodal portion to said hip tripodal portion;
   a knee post fixedly attached to said knee tripodal portion, said knee post vertically extending orthogonally away from said horizontally planar base;
   a hip post fixedly attached to said hip tripodal portion, said hip post vertically extending orthogonally away from said horizontally planar base;
   a knee bar connected to said knee post, said knee bar secured to said knee post; and
   a hip bar connected to said hip post, said hip bar secured to said hip post.

2. An apparatus for testing the entire lower extremity function of a human body, the apparatus comprising:
   a horizontally planar base, comprising:
      a knee tripodal portion;
      a hip tripodal portion; and
      a variable length connector adjustably coupling said knee tripodal portion to said hip tripodal portion;
   a knee post fixedly attached to said knee tripodal portion, said knee post vertically extending orthogonally away from said horizontally planar base;
   a hip post fixedly attached to said hip tripodal portion, said hip post vertically extending orthogonally away from said horizontally planar base;
   a knee bar adjustably connected to said knee post, said knee bar releasably secured to said knee post by a locking fastener; and
   a hip bar adjustably connected to said hip post, said hip bar releasably secured to said hip post by a locking fastener.

3. An apparatus for testing the entire lower extremity function of a human body in accordance with claim 2 wherein said knee tripodal portion of said horizontally planar base is releasably secured to said variable length connector by a locking fastener.

4. An apparatus for testing the entire lower extremity function of a human body in accordance with claim 2 wherein said hip tripodal portion of said horizontally planar base is releasably secured to said variable length connector by a locking fastener.

5. An apparatus for testing the entire lower extremity function of a human body in accordance with claim 2 wherein said variable length connector adjustably couples said knee tripodal portion to said hip tripodal portion with a mechanical, hydraulic or electrical adjustment mechanism.

6. An apparatus for testing the entire lower extremity function of a human body in accordance with claim 2 wherein said knee tripodal portion of said horizontally planar base comprises:
   a first central hollow pole having a diameter;
   a first lateral supporting pole fixedly attached to said first central hollow pole, said first lateral supporting pole extending perpendicularly away from said first central hollow pole; and
   a second lateral supporting pole fixedly attached to said first central hollow pole, said second lateral supporting pole extending perpendicularly away from said first central hollow pole.

7. An apparatus for testing the entire lower extremity function of a human body in accordance with claim 2 wherein said knee tripodal portion further comprises:
   a second foot placement guide of said second lateral supporting pole comprising:
      a second rod perpendicularly transversing through said second lateral supporting pole of said knee tripodal portion;
      a second end extending toward said fourth lateral supporting pole of said hip tripodal portion; and
      a second solid plate secured to said second end of said second rod.

8. An apparatus for testing the entire lower extremity function of a human body in accordance with claim 2 wherein said knee tripodal portion further comprises:
   a second foot placement guide of said second lateral supporting pole comprising:
      a second rod perpendicularly transversing through said second lateral supporting pole of said knee tripodal portion;
      a second end extending toward said fourth lateral supporting pole of said hip tripodal portion; and a second solid plate secured to said second end of said second rod; and a first foot placement guide of said first lateral supporting pole comprising:
- a first rod perpendicularly transversing through said first lateral supporting pole of said knee tripodal portion;
- a first end extending toward said third lateral supporting pole of said hip tripodal portion; and
- a first solid plate secured to said first end of said first rod.

9. An apparatus for testing the entire lower extremity function of a human body in accordance with claim 2 wherein said hip tripodal portion of said horizontally planar base comprises:
- a second central hollow pole having a diameter;
- a third lateral supporting pole fixedly attached to said second central hollow pole, said third lateral supporting pole extending perpendicularly away from said second central hollow pole; and
- a fourth lateral supporting pole fixedly attached to said second central hollow pole, said fourth lateral supporting pole extending perpendicularly away from said second central hollow pole.

10. An apparatus for testing the entire lower extremity function of a human body in accordance with claim 6 wherein said knee tripodal portion is connected to, or mounted on, a flat triangular knee tripodal support plate.

11. An apparatus for testing the entire lower extremity function of a human body in accordance with claim 9 wherein said hip tripodal portion is connected to, or mounted on, a flat triangular hip tripodal support plate.

12. An apparatus for testing the entire lower extremity function of a human body in accordance with claim 6 wherein said first lateral supporting pole and said second lateral supporting pole are each equipped with a stabilizer.

13. An apparatus for testing the entire lower extremity function of a human body in accordance with claim 9 wherein said third lateral supporting pole and said fourth lateral supporting pole are each equipped with a stabilizer.

14. An apparatus for testing the entire lower extremity function of a human body in accordance with claim 12 wherein said stabilizer further comprises:
- a locking hinge mounted to each of said lateral supporting poles;
- a shaft having a first end hingedly connected to said locking hinge and a second end opposing said first end; and
- a footplate fixedly attached to said second end of said shaft.

15. An apparatus for testing the entire lower extremity function of a human body in accordance with claim 13 wherein said stabilizer further comprises:
- a locking hinge mounted to each of said lateral supporting poles;
- a shaft having a first end hingedly connected to said locking hinge and a second end opposing said first end; and
- a footplate fixedly attached to said second end of said shaft.

16. An apparatus for testing the entire lower extremity function of a human body in accordance with claim 6 wherein said knee tripodal portion has a generally cross shape.

17. An apparatus for testing the entire lower extremity function of a human body in accordance with claim 9 wherein said hip tripodal portion has a generally cross shape.

18. An apparatus for testing the entire lower extremity function of a human body in accordance with claim 6 wherein said variable length connector is a cylindrical tube having a diameter that is less than said diameter of said first central hollow pole of said knee tripodal portion.

19. An apparatus for testing the entire lower extremity function of a human body in accordance with claim 18 wherein said first central hollow pole is releasably secured to said cylindrical tube of said variable length connector by a locking fastener.

20. An apparatus for testing the entire lower extremity function of a human body in accordance with claim 9 wherein said variable length connector is a cylindrical tube having an exterior surface, a stippling on said exterior surface, and a diameter that is less than said diameter of said second central hollow pole of said hip tripodal portion.

21. An apparatus for testing the entire lower extremity function of a human body in accordance with claim 20 wherein said second central hollow pole is releasably secured to said cylindrical tube of said variable length connector by a locking fastener.

22. An apparatus for testing the entire lower extremity function of a human body in accordance with claim 6 wherein said knee post fixedly attached to said first central hollow pole of said knee tripodal portion, said knee post extending orthogonally away from said horizontally planar base.

23. An apparatus for testing the entire lower extremity function of a human body in accordance with claim 22 wherein said knee post is a first hollow cylindrical tube having a diameter.

24. An apparatus for testing the entire lower extremity function of a human body in accordance with claim 22 wherein said knee post is of multilevel telescopic construction vertically adjusted by a manual, mechanical, hydraulic or electrical mechanism.

25. An apparatus for testing the entire lower extremity function of a human body in accordance with claim 9 wherein said hip post fixedly attached to said second central hollow pole of said hip tripodal portion, said hip post extending orthogonally away from said horizontally planar base.

26. An apparatus for testing the entire lower extremity function of a human body in accordance with claim 25 wherein said hip post is a second hollow cylindrical tube having a diameter.

27. An apparatus for testing the entire lower extremity function of a human body in accordance with claim 25 wherein said hip post is of multilevel telescopic construction vertically adjusted by a manual, mechanical, hydraulic or electrical mechanism.

28. An apparatus for testing the entire lower extremity function of a human body in accordance with claim 23 wherein said knee bar has a diameter that is less than said diameter of said first hollow cylindrical tube of said knee post.

29. An apparatus for testing the entire lower extremity function of a human body in accordance with claim 24 wherein said hip bar has a diameter that is less than said diameter of said second hollow cylindrical tube of said hip post.

30. An apparatus for testing the entire lower extremity function of a human body in accordance with claim 23 wherein said knee bar comprises:
- a first vertical segment, said first vertical segment releasably secured to said knee post by a locking fastener;
- a first horizontal segment having a cushion attached to the exterior of said first horizontal segment; and a first elbow bend interconnecting said first horizontal segment with said first vertical segment.

31. An apparatus for testing the entire lower extremity function of a human body in accordance with claim 30 wherein said first elbow bend interconnects said first horizontal segment with said first vertical segment forming a general L shape.

32. An apparatus for testing the entire lower extremity function of a human body in accordance with claim 30 wherein said first elbow bend interconnects said first horizontal segment with said first vertical segment forming a general T shape.

33. An apparatus for testing the entire lower extremity function of a human body in accordance with claim 30 wherein said first vertical segment has a diameter that is less than said diameter of said first hollow cylindrical tube of said knee post.

34. An apparatus for testing the entire lower extremity function of a human body in accordance with claim 33 wherein said first vertical segment is inserted and telescopically received within said first hollow cylindrical tube of said knee post.

35. An apparatus for testing the entire lower extremity function of a human body in accordance with claim 34 wherein said first vertical segment having an exterior surface and a stippling on said exterior surface of said first vertical segment.

36. An apparatus for testing the entire lower extremity function of a human body in accordance with claim 26 wherein said hip bar comprises:
   a second vertical segment, said second vertical segment releasably secured to said hip post by a locking fastener;
   a second horizontal segment having a cushion attached to the exterior of said second horizontal segment; and
   a second elbow bend interconnecting said second horizontal segment and said second vertical segment.

37. An apparatus for testing the entire lower extremity function of a human body in accordance with claim 36 wherein said second elbow bend interconnects said second horizontal segment with said second first vertical segment forming a general L shape.

38. An apparatus for testing the entire lower extremity function of a human body in accordance with claim 36 wherein said second elbow bend interconnects said second horizontal segment with said second vertical segment forming a general T shape.

39. An apparatus for testing the entire lower extremity function of a human body in accordance with claim 36 wherein said second vertical segment has a diameter that is less than said diameter of said second hollow cylindrical tube of said hip post.

40. An apparatus for testing the entire lower extremity function of a human body in accordance with claim 39 wherein said second vertical segment is inserted and telescopically received within said second hollow cylindrical tube of said hip post.

41. An apparatus for testing the entire lower extremity function of a human body in accordance with claim 40 wherein said second vertical segment having an exterior surface and a stippling on said exterior surface of said second vertical segment.

42. An apparatus for testing the entire lower extremity function of a human body in accordance with claim 2 wherein said locking fasteners are locking pins.

43. An apparatus for testing the entire lower extremity function of a human body in accordance with claim 2 wherein said locking fasteners are locking pins.

44. An apparatus for testing the entire lower extremity function of a human body in accordance with claim 3 wherein said locking fastener is a locking pin.

45. An apparatus for testing the entire lower extremity function of a human body in accordance with claim 4 wherein said locking fastener is a locking pin.

46. An apparatus for testing the entire lower extremity function of a human body in accordance with claim 19 wherein said locking fastener is a locking pin.

47. An apparatus for testing the entire lower extremity function of a human body in accordance with claim 21 wherein said locking fastener is a locking pin.

48. A method for testing the entire lower extremity function of a patient utilizing a single leg squat apparatus having a horizontally planar base, a variable height knee bar and a variable height hip bar, said method comprising the steps of:
   confirming a patient's range of motion for a desired degree of knee flexion;
   adjusting the height of the knee bar so that the midline of the patient's patella is positioned substantially adjacent to the midline of the knee bar at the desired degree of knee flexion;
   adjusting the height of the hip bar so that the patient's ischial tuberosity is positioned substantially adjacent to the midline of the hip bar at the desired degree of knee flexion;
   performing a single leg squat on a test leg so that the patient's knee lightly contacts the knee bar without unloading on the knee bar and the patient's ischial tuberosity lightly contacts the hip bar without unloading on the hip bar; and
   returning the test leg to a full extension.

49. A method for testing the entire lower extremity function of a patient in accordance with claim 48 wherein prior to said step of adjusting the height of the knee bar, said method comprises:
   standardizing the patient's desired degree of knee flexion based on the angle of the patient's ankle dorsiflexion.

50. A method for testing the entire lower extremity function of a patient in accordance with claim 48 wherein prior to said step of performing, said method further comprises:
   positioning the patient's test leg in a full extension and flexing the patient's non-test leg at the hip, knee and ankle.

51. A method for testing the entire lower extremity function of a patient in accordance with claim 48 further comprising:
   performing at least one warm-up repetition of the single leg squat while holding onto a support with each of the patient's upper extremity for balance;
   resting for a first period;
   performing at least one warm-up repetition of the single leg squat without holding onto the support;
   resting for a second period; and
   performing a maximum number of repetitions of the single leg squat in a pre-determined period without holding onto the support.

52. A method for testing the entire lower extremity function of a patient in accordance with claim 48 further comprising:
   repeating said steps of performing at least one warm-up repetition of the single leg squat while holding onto a support through said step of performing a maximum number of repetitions for the patient's non-test leg.

* * * * *